(12) United States Patent
Bluestein et al.

(10) Patent No.: US 9,655,720 B2
(45) Date of Patent: May 23, 2017

(54) POLYMERIC HEART VALVE

(71) Applicants: THE RESEARCH FOUNDATION FOR THE STATE UNIVERSITY OF NEW YORK, Albany, NY (US); THE ARIZONA BOARD OF REGENTS ON BEHALF OF THE UNIVERSITY OF ARIZONA, Tucson, AZ (US)

(72) Inventors: Danny Bluestein, Melville, NY (US); Thomas E. Claiborne, Bayport, NY (US); Marvin J. Slepian, Tucson, AZ (US)

(73) Assignees: The Research Foundation for The State University of New York, Albany, NY (US); The Arizona Board of Regents on Behalf of the University of Arizona, Tucson, AZ (US)

( * ) Notice: Subject to any disclaimer, the term of this patent is extended or adjusted under 35 U.S.C. 154(b) by 0 days.

(21) Appl. No.: 14/351,455

(22) PCT Filed: Oct. 12, 2012

(86) PCT No.: PCT/US2012/059845
§ 371 (c)(1),
(2) Date: Apr. 11, 2014

(87) PCT Pub. No.: WO2013/055977
PCT Pub. Date: Apr. 18, 2013

(65) Prior Publication Data
US 2014/0303724 A1    Oct. 9, 2014

Related U.S. Application Data

(60) Provisional application No. 61/546,832, filed on Oct. 13, 2011.

(51) Int. Cl.
*A61F 2/24* (2006.01)

(52) U.S. Cl.
CPC .......... *A61F 2/2415* (2013.01); *A61F 2/2412* (2013.01); *A61F 2/2418* (2013.01); *A61F 2250/0036* (2013.01)

(58) Field of Classification Search
CPC ............................ A61F 2/2415; A61F 2/2412
See application file for complete search history.

(56) References Cited

U.S. PATENT DOCUMENTS

| 6,953,332 B1 * | 10/2005 | Kurk et al. | 425/275 |
| 2002/0045936 A1 * | 4/2002 | Moe | A61F 2/2412 |
| | | | 623/2.17 |

(Continued)

FOREIGN PATENT DOCUMENTS

| SU | 1144216 A | 10/1987 |
| WO | WO 93/18721 A1 | 9/1993 |

(Continued)

OTHER PUBLICATIONS

Supplementary European Search Report dated Feb. 27, 2015 received in related Application No. 12840473.8.

(Continued)

*Primary Examiner* — Katrina Stransky
*Assistant Examiner* — Wade P Schutte
(74) *Attorney, Agent, or Firm* — Scully, Scott, Murphy & Presser, P.C.

(57) ABSTRACT

A polymeric valve which may include a heart valve, and also may include a trileaflet heart valve includes a stent having a base and a plurality of outwardly extending posts from the base and equidistant from each other. A plurality of leaflets each connected to a corresponding one of the posts at one end, and each of the leaflets connected to the base. Each of the leaflets having an operative end opposite the end con- (Continued)

nected to the post, and the operative ends of the leaflets being biased in a closed position such that the operative ends abut each other. The operative ends are configured to rhythmically open and close in relation to each other, and the leaflets include multiple cross sectional thicknesses at different portions of the leaflets.

25 Claims, 13 Drawing Sheets
(10 of 13 Drawing Sheet(s) Filed in Color)

(56) References Cited

U.S. PATENT DOCUMENTS

| 2003/0078652 | A1* | 4/2003 | Sutherland | A61F 2/2412 623/2.12 |
|---|---|---|---|---|
| 2003/0097175 | A1 | 5/2003 | O'Connor et al. | |
| 2003/0114924 | A1 | 6/2003 | Moe | |
| 2006/0241744 | A1 | 10/2006 | Beith | |
| 2007/0118210 | A1 | 5/2007 | Pinchuk | |
| 2007/0154513 | A1* | 7/2007 | Atanasoska et al. | 424/423 |
| 2011/0257738 | A1* | 10/2011 | Corbett et al. | 623/2.12 |
| 2012/0065729 | A1* | 3/2012 | Pintor et al. | 623/2.11 |

FOREIGN PATENT DOCUMENTS

| WO | WO 98/32400 A1 | 7/1998 |
|---|---|---|
| WO | WO 01/05334 A1 | 1/2001 |
| WO | WO 02/100301 A1 | 12/2002 |
| WO | WO 2009/111241 A2 | 9/2009 |

OTHER PUBLICATIONS

International Search Report dated Jan. 17, 2013 issued in PCT/US2012/059845.

* cited by examiner

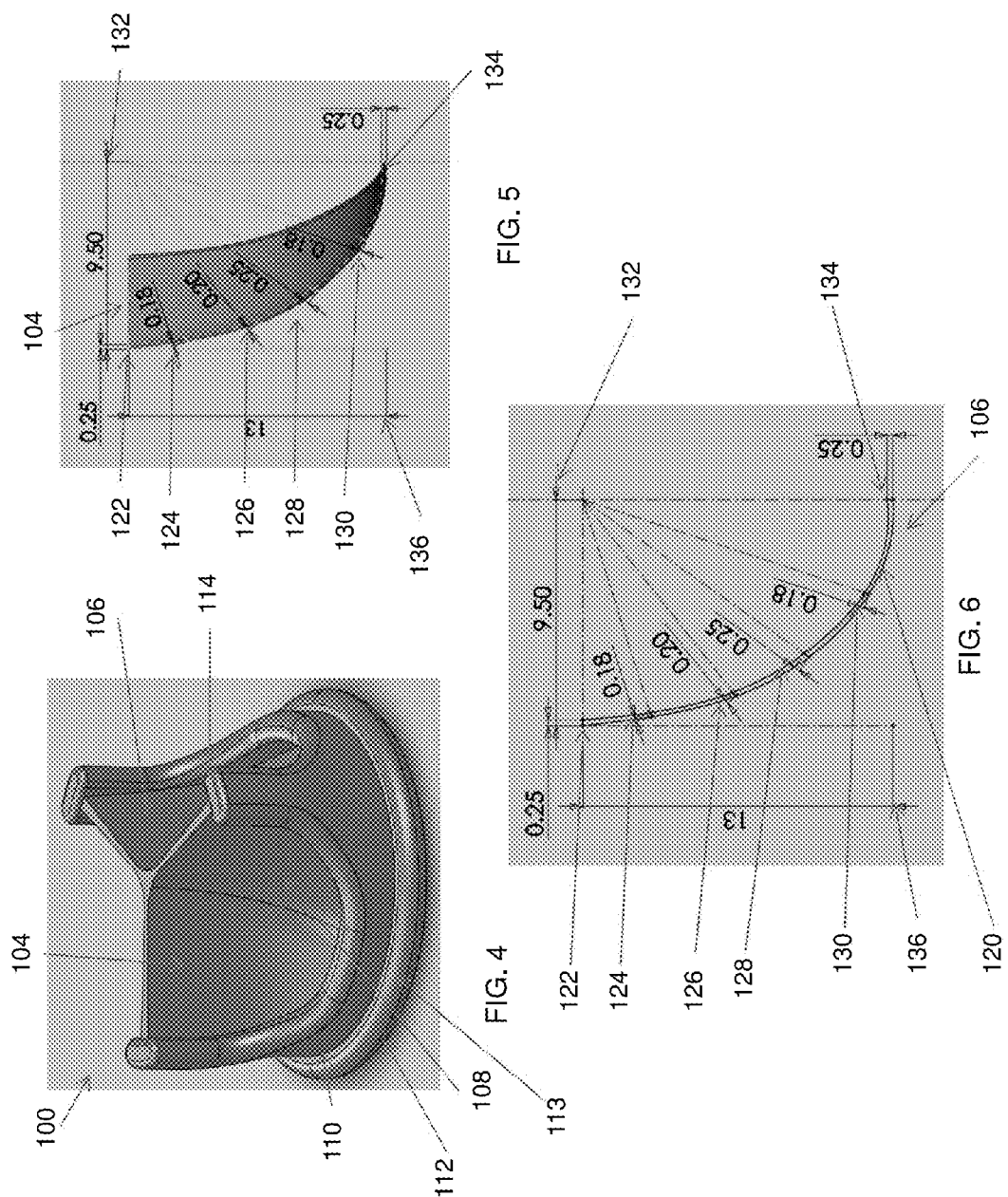

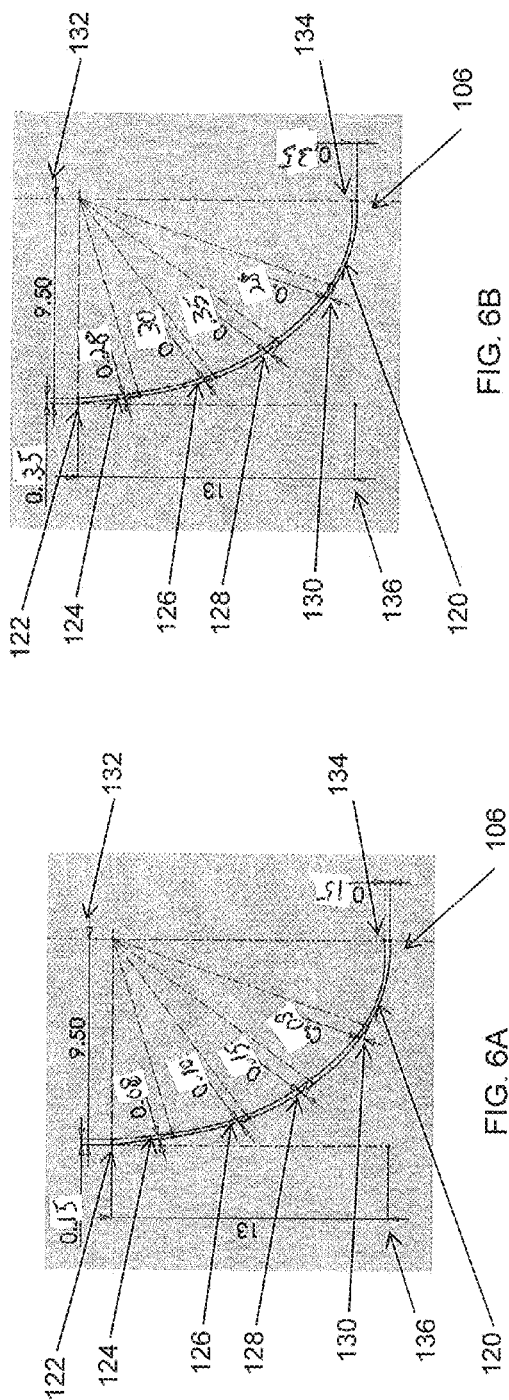
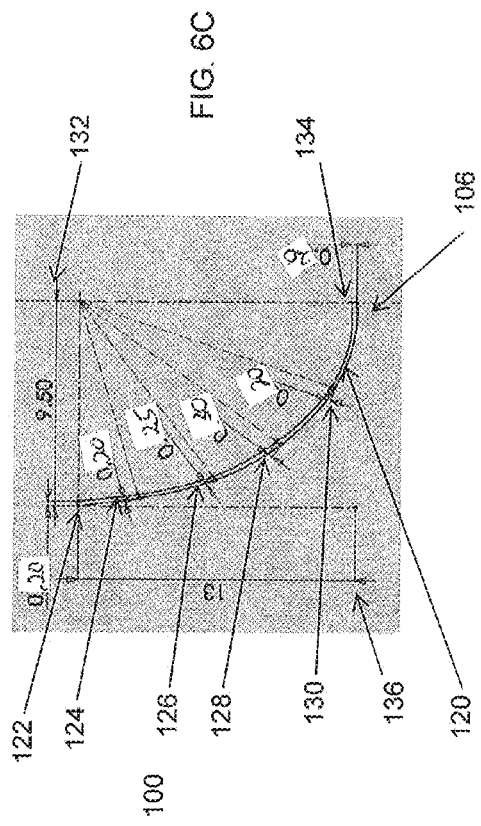
FIG. 6A
FIG. 6B
FIG. 6C

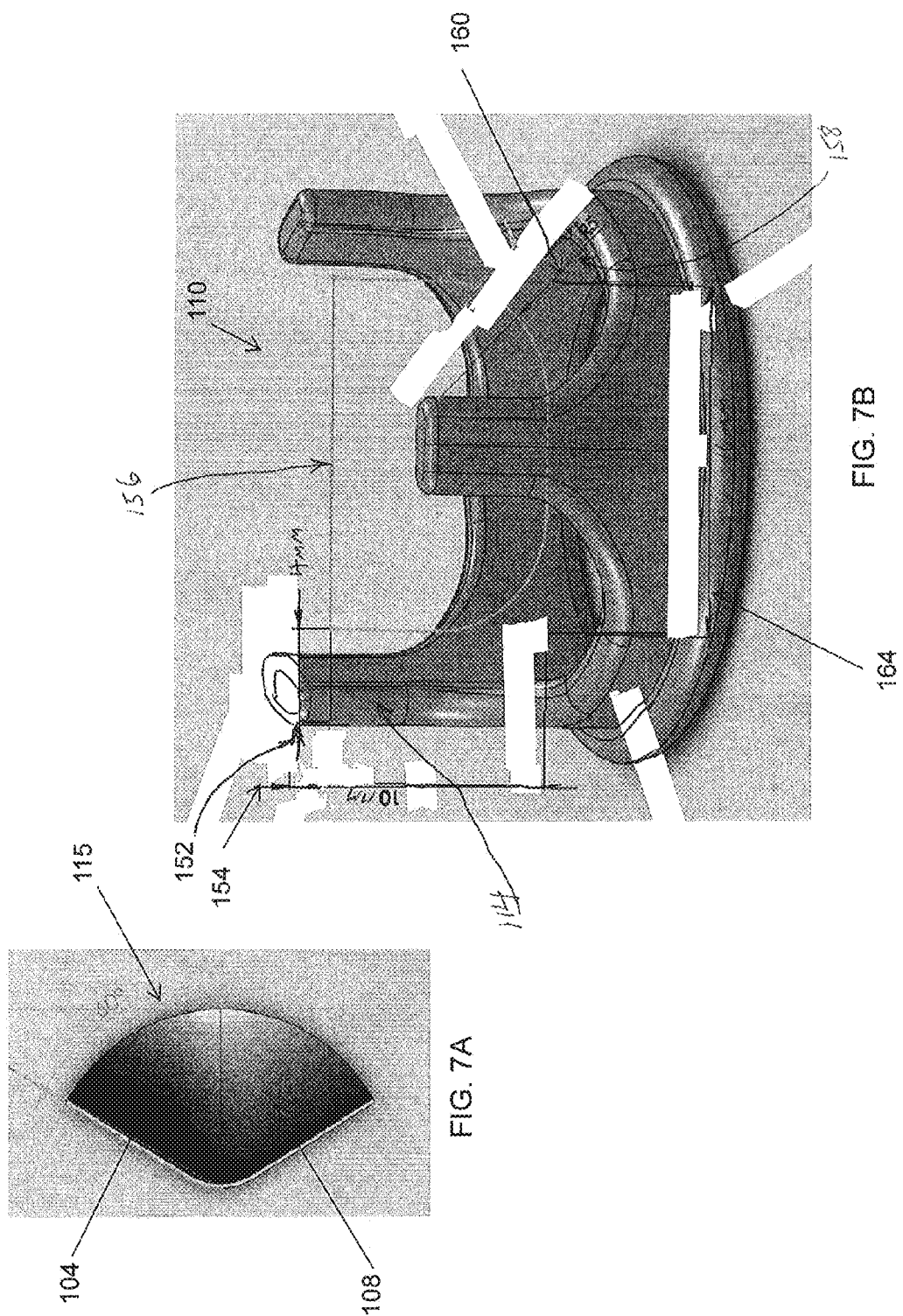

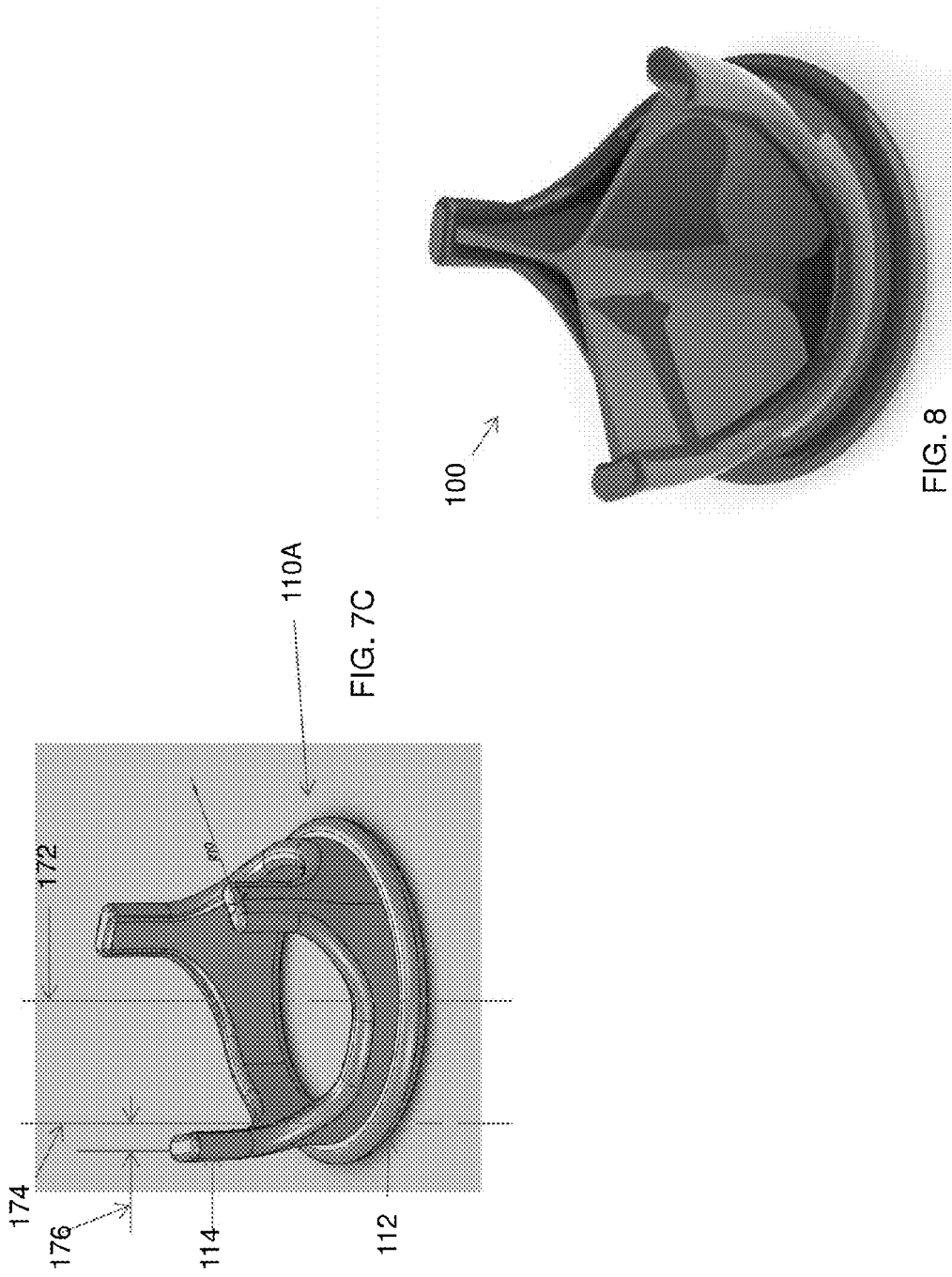

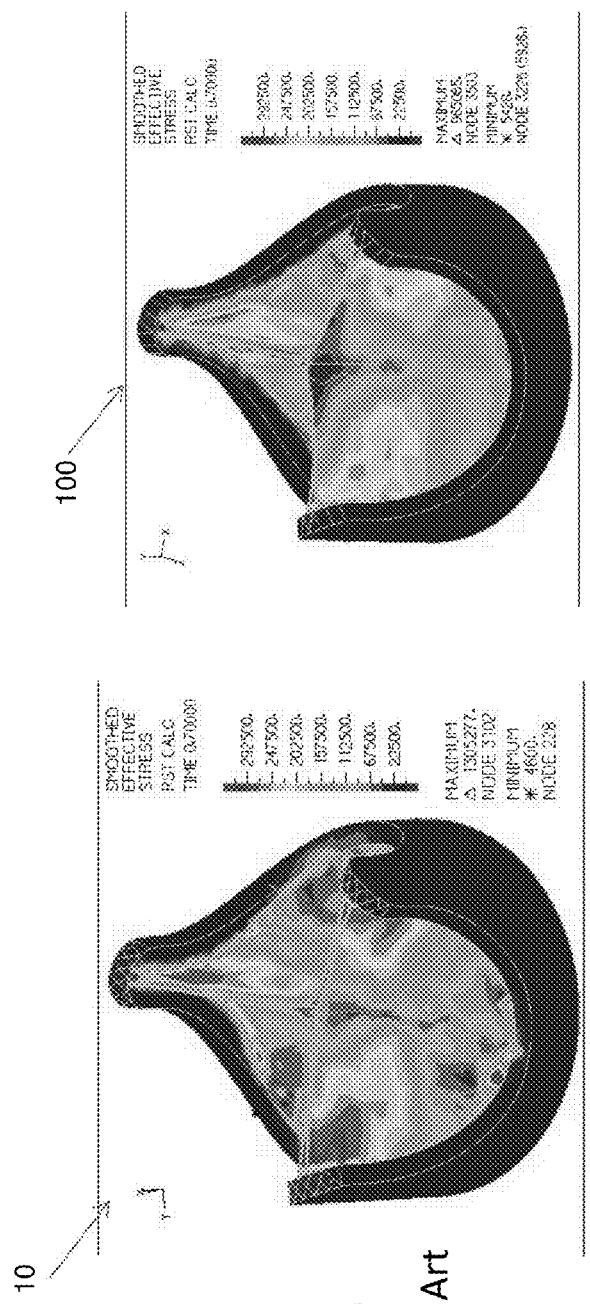
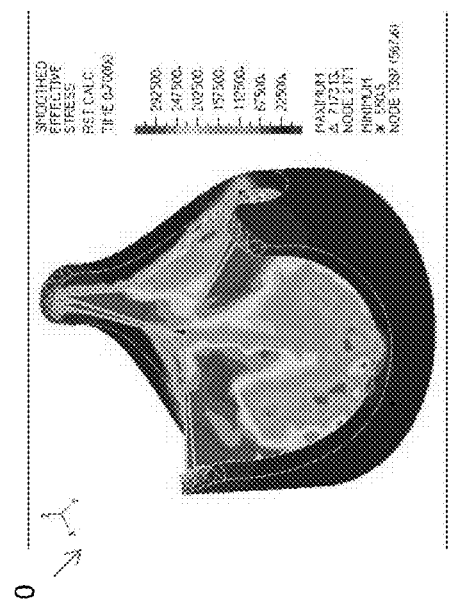
FIG. 9 Prior Art
FIG. 10
FIG. 11 Prior Art

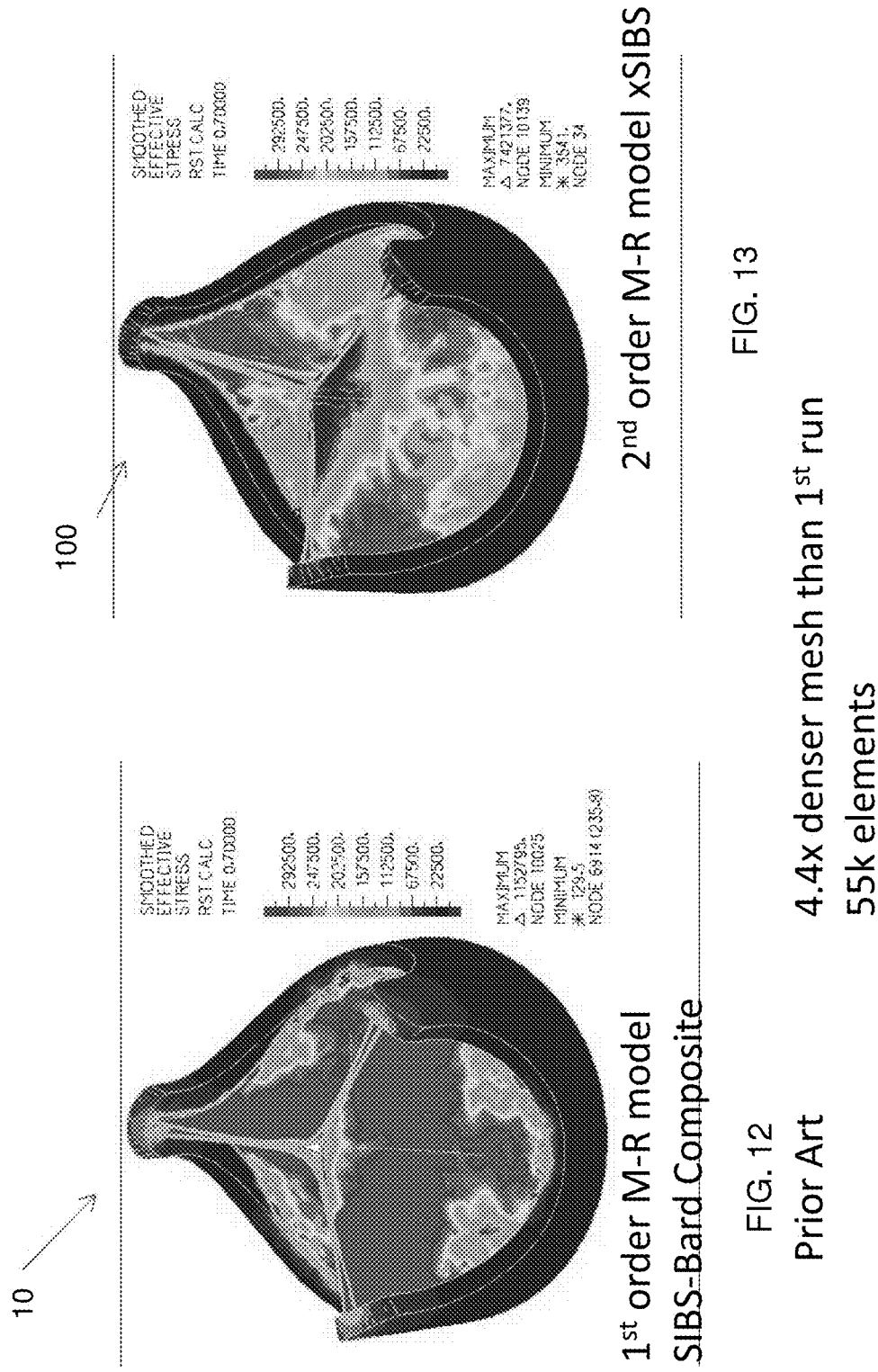

2nd order M-R model xSIBS

1st order M-R model
SIBS-Bard Composite

Mesh 170k elements
13.6 x denser than 1st run
(end time here is 0.24 s
Optimized sim. crashed)

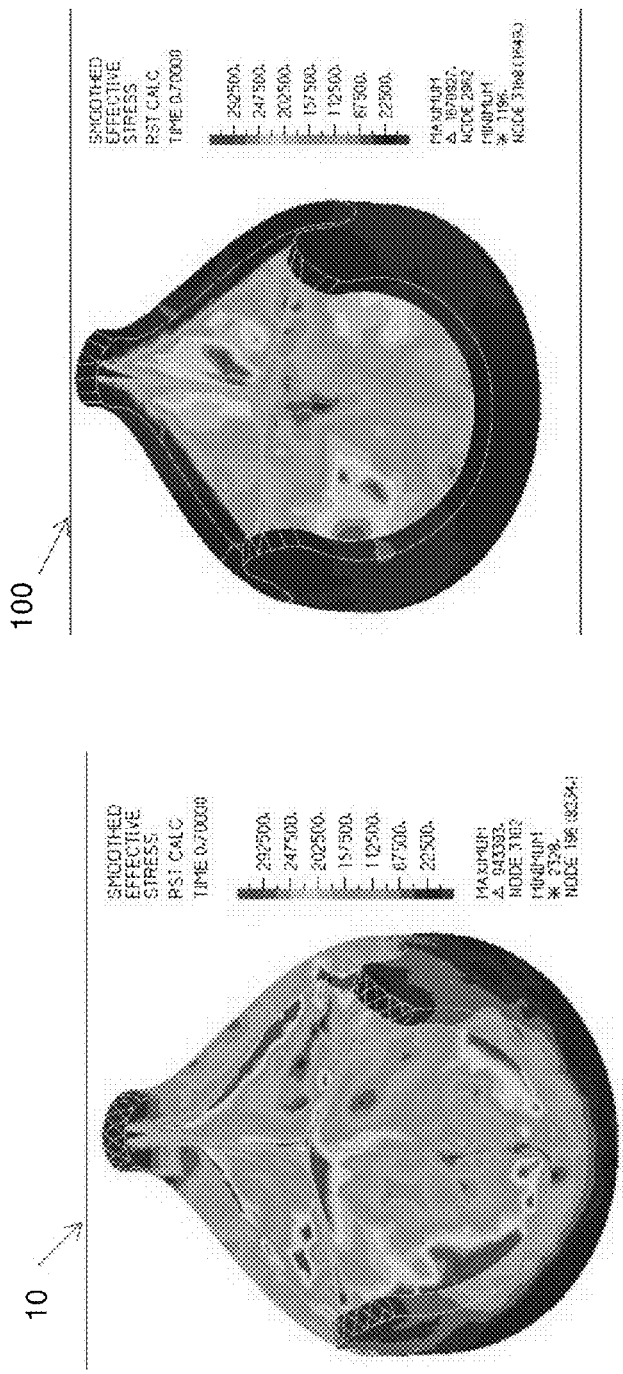

Both valves with optimized xSIBS leaflets

Coarse mesh xSIBS Optimized leaflets in redesigned stent
Systolic pressure load of 10 mmHg
Coarse mesh (left) dense mesh (right)

ial reaction. Further, the above heart valve requires a multilayer composite approach that is undesirably complex to manufacture and expensive. It also does not allow for fine tuning of the leaflet thickness to improve flexibility and durability.

POLYMERIC HEART VALVE

CROSS-REFERENCE TO RELATED APPLICATIONS

This application claims the benefit of U.S. Provisional Application No. 61/546,832 filed on Oct. 13, 2011, the entire contents of which are incorporated herein by reference.

STATEMENT REGARDING FEDERALLY SPONSORED RESEARCH OR DEVELOPMENT

This invention was made with government support under grant number EB012487 awarded by the National Institute of Health. The government has certain rights in the invention.

BACKGROUND OF THE INVENTION

1. Field of the Invention

The present invention generally relates to implantable prosthetic devices, and more particularly, the present invention relates to an implantable prosthetic heart valve and a method for manufacturing thereof.

2. Description of Related Art

Replacement valves in a patient and in machines for mimicking valves in a patient are known in the medical field. For example, valvular heart disease (VHD) remains a significant public health issue affecting 1-2% of Americans with an estimated 2-4% of people over the age of 65 suffering from aortic valve stenosis. Currently, when extensive heart valve damage has occurred in a patient's heart, for example from heart disease or a birth defect, one remedy is to replace the heart valve surgically. Current treatment includes open-heart surgical replacement of the diseased valve with either mechanical or tissue prosthetic heart valves (PHV). The replacement heart valve may be an artificial device or an animal tissue valve (e.g., bovine pericardium or porcine aortic valve). For example, one type of heart valve which has been the subject of replacement valves are aortic valves. Presently, artificial (mechanical) heart valves are not as prevalently used as animal tissue valves. One reason is artificial valves such as polymer PHVs are unsatisfactorily susceptible to damage caused by stresses from flexing and operation during use, i.e., material fatigue. Since 1960, various devices and techniques have been used for replacement valves and delivery or implantation of the valve.

Referring to FIGS. 1-3, a prior art trileaflet heart valve 10 includes three leaflets 14, 16, 18, and a stent structure 20 having three posts 22. The stent structure 20 supports a multilayer composite polymeric membrane that is a flat sheet membrane sewn into the shape of three leaflets 14, 16, 18, each having a uniform thickness. The one-piece multilayer composite polymeric membrane of the leaflets 14, 16, 18 is composed of a porous polymeric structure (e.g. a knit, weave, braid) sandwiched between two outer polymer layers. An example of such a one-piece multilayer composite polymeric membrane and heart valve as described is US Patent Application publication 2007/0118210 (pub. date May 24, 2007), Ser. No. 11/561,069, filed on Nov. 17, 2006.

One disadvantage of the above prior art heart valve is undesirable stress wear on the leaflets results in fatigue of the leaflets. The polymer in the prior art was a thermoplastic elastomer with low tensile strength and was prone to significant creep. The embedded mesh was designed to add strength. However, in animal testing the polymer creep exposed the underlying mesh to blood and caused an adverse reaction. Further, the above heart valve requires a multilayer composite approach that is undesirably complex to manufacture and expensive. It also does not allow for fine tuning of the leaflet thickness to improve flexibility and durability. A disadvantage of using animal tissue in replacement heart valves is that chemically fixed animal tissue valves require animal tissue sourcing, handling, processing, sterilization and packaging. Further, other disadvantages from current heart valve implantation are present from the risk to a patient receiving animal tissue heart valves, that is the implanting of xenografts, because of the differences in tissue degeneration, or tissue lifespan, between species of animals and humans, and also the possibility of transfer of diseases from the animal to a human. Also, the durability of animal tissue valves is highly dependent upon the application and the health and age of the patient. There has therefore been a long felt need in the industry for a valve, and particularly a heart valve to remedy the disadvantages described above. Additionally, mechanical valves require lifelong anticoagulant drug therapy which includes significant risk of bleeding and stroke. Polymeric trileaflet valves may eliminate the disadvantages of current heart valve prosthetics.

SUMMARY OF THE INVENTION

It would be desirable to provide a valve for use in heart valve replacement that eliminates the need for animal tissue sourcing, handling, processing, sterilization and packaging, and thereby eliminates any risks to patients involved in implanting xenografts. Further, it would be desirable to provide a replacement valve of increased durability which is not dependent on the health and age of the patient. It would further be advantageous to provide a polymeric heart valve, which can decrease the costs for heart valve replacement. Also, a need exists in the art for a prosthetic valve, and for example, specifically a trileaflet valve, which has improved durability and is less susceptible to fatigue stress. Also, a need exists for the reduction or elimination for the need for anticoagulant drug therapy in prosthetic heart valve recipients. Further, it would be desirable for a prosthetic valve to include a polymer PHVs which combines improved durability with low thrombogenicity.

In an aspect of the invention, a polymeric valve which may include a heart valve, and also may include a trileaflet heart valve includes a stent having a base and a plurality of outwardly extending posts from the base and equidistant from each other. A plurality of leaflets each connected to a corresponding one of the posts at one end, and each of the leaflets connected to the base. Each of the leaflets having an operative end opposite the end connected to the post, and the operative ends of the leaflets being biased in a closed position such that the operative ends abut each other. The operative ends are configured to rhythmically open and close in relation to each other, and the leaflets include multiple cross sectional thicknesses at different portions of the leaflets for optimized flexibility and durability.

BRIEF DESCRIPTION OF THE DRAWINGS

These and other objects, features and advantages of the present invention will become apparent from the following detailed description of illustrative embodiments thereof, which is to be read in connection with the accompanying drawings. The various features of the drawings are not to scale as the illustrations are for clarity in facilitating one skilled in the art in understanding the invention in conjunction with the detailed description. This patent application (or patent) contains at least one drawing executed in color. Copies of this patent or patent application publication with color drawing(s) will be provided by the Office upon request and payment of the necessary fee. In the drawings:

FIG. 4 is an isometric view of a trileaflet heart valve according to an embodiment of the invention;

FIG. 5 is a perspective view of a leaflet of the heart valve shown in FIG. 4 depicting the curvature of the leaflet;

FIG. 6 is a cross-sectional view of the center of a leaflet showing representative dimensions of the thicknesses of the leaflet along an operative end of the leaflet;

FIG. 6A is a side elevational view of another embodiment of a leaflet as compared to FIG. 6, showing thicknesses of the leaflet along an operative end of the leaflet;

FIG. 6B is a side elevational view of another embodiment of a leaflet as compared to FIGS. 6 and 6A, showing thicknesses of the leaflet along an operative end of the leaflet;

FIG. 6C is a side elevational view of another embodiment of a leaflet showing thicknesses of the leaflet along an operative end of the leaflet;

FIG. 7A is a top view of two of the leaflets of the valve shown in FIG. 4;

FIG. 7B is an isometric view of the stent shown in FIG. 4;

FIG. 7C is isometric view of another embodiment of a stent having post inclined outwardly;

FIG. 8 is an isometric view of the heart valve shown in FIG. 4; and

FIGS. 9-21 are color diagrams of embodiment of valves according to the present invention compared to prior art valves depicting stress effects on the leaflets using different colors via finite element analysis using accurate material models based upon valve material uniaxial tensile tests with red being high stress.

DETAILED DESCRIPTION OF THE INVENTION

Figure 2:
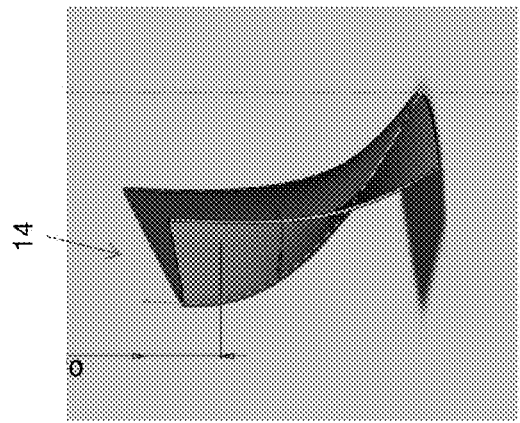
FIG. 2 is an isometric view of a leaflet of the prior art valve shown in FIG. 1 depicting the curvature of the leaflet.
Figure 1:
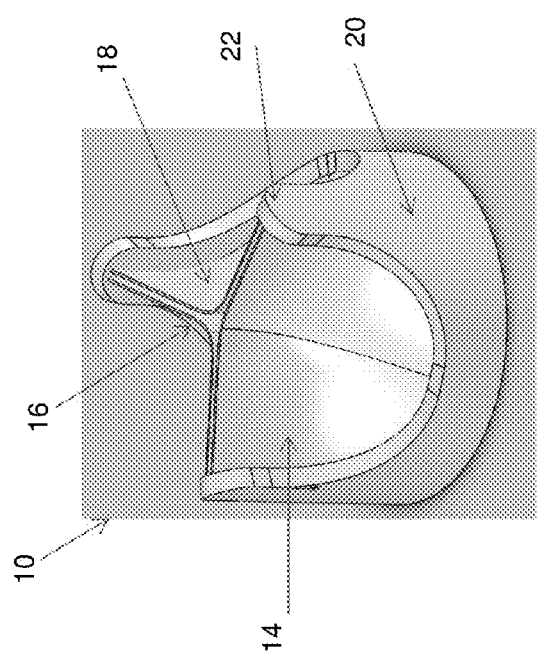
FIG. 1 is an isometric view of a prior art trileaflet heart valve.
Figure 3:
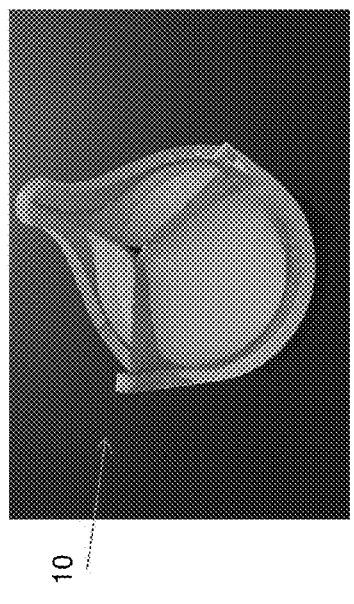
FIG. 3 is an isometric view of the prior art heart valve shown in FIG. 1.
Figures 14, 15:
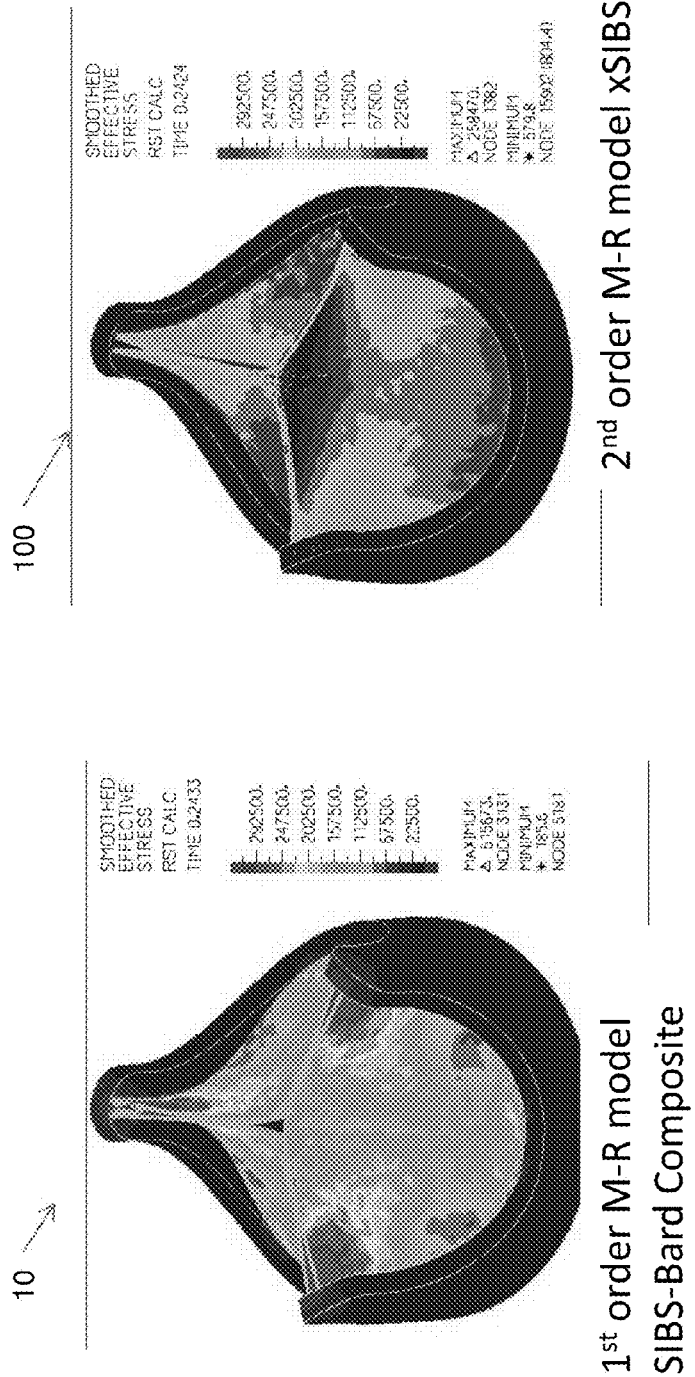

Referring to FIGS. 4-6, an embodiment according to the invention of a trileaflet heart valve 100 is shown. The heart valve 100 includes three leaflets 104, 106, 108. The heart valve further includes a stent 110 having a circular base 112 and three posts 114 extending outwardly from the base 112. The posts 114 are each offset from vertical by 1 mm making an inlet orifice of the valve 19 mm ID, and an outlet orifice 21 mm of the valve. This increases the effective orifice area and reduces the stresses in the leaflets.

A bottom ridge 113 of the base extends circumferentially around the base 112 forming the hemispherical bottom ridge 113. The posts 114 are positioned in spaced relation to each other to provide a wide stent orifice. The post positioning in the present invention improves hemodynamics as a result of the widened orifice of the stent. The heart valve 100 is designed to mimic the native aortic valve in form and function. The posts 114 include a substantially rectangular top portion 115 which has rounded edges. The heart valve stent 110 has rounded edges for improved hemodynamics, which includes the area at the top of the posts, and the upper edge along the perimeter of the stent.

The heart valve 100 leaflets 104, 106, 108 and the stent 110 are injection molded as a single part. The leaflets are composed of a singular material, and not constructed from a composite of materials. In one embodiment of the invention, valves are molded from custom designed molds using a vacuum oven and hot-press for injection molding. Computer aided design (CAD) software may be used to create solid models of valve prototypes and valve molds. A left heart simulator (LHS) can be used for accurate hydrodynamic assessment of the heart valve for meeting FDA standards. An accelerated life cycle tester can be used for durability assessment of the heart valves, such as from Vivitro Labs. Such a machine can simulate 5 years of use in 4 months at 20 Hz. A digital particle image velocimetry (DPIV) system can be used for the validation of numerical blood analog flow results from the LHS. Full prototype platelet activation can be measured in a small volume flow loop (left ventricular assist) device.

The valve 100 diameter is variable based upon patient valve dimensions. The valve 100 may be manufactured in several sizes for a specific patient fit. It is understood that the valve 100 can be manufactured to fit in all nominal human aortic valve positions, in the range of approximately 15-27 mm tissue annulus diameter (TAD). Further, the valve 100 diameter and all other dimensions are proportionally variable based upon patient aortic root dimensions. Thus, all the dimensions of the valve of the present disclosure, may proportionally vary when a different valve size is needed and manufactured, e.g., the leaflets thickness tapering dimensions (which results in cross sectional dimensions shown in FIGS. 6, 6A, 6B, 6C), will proportionally vary according to the size of the valve, as well as the length and width dimensions of the leaflets and other parts and sections of the valve.

In another embodiment of the invention, the valve stent 110 may have a metal reinforcing frame 200 embedded for added stiffness where needed. Acceptable types of metal for reinforcing the stent may include, for example, stainless steel. In an alternate embodiment, the reinforcing frame 200 can be fabricated from a biologically compatible material or composite that provides the rigidity of e.g. stainless steel.

The material of the valve is a polymer that has not been previously applied to prosthetic heart valves. The polymer may enhance durability and hemocompatibility over chemically fixed animal tissue and competitive polymers. The polymer useful in the manufacture of the valve of the invention is a formulation provided by Innovia®, LLC Miami, Fla. that is a thermally cross-linkable formulation of their thermoplastic elastomer-poly(styrene-isobutylene-styrene) or SIBS. SIBS has physical properties that overlap polyurethane and silicone rubber. SIBS has been shown to be hydrolytically, enzymatically, and oxidatively stable in vivo. The infusible and insoluble cross-linkable thermoset formulation is called xSIBS. It is believed that xSIBS has enhanced durability over SIBS because the cross-linking of the polymer chains adds strength and reduces or eliminates creep (time dependent change in strain under a constant load below the yield stress). Altering the ratio of SIBS constituents, styrene and isobutylene, will alter the hardness or softness of the material. In one embodiment, xSIBS may include about 22% styrene. Other polymers may also be applicable in the heart valve of the present invention.

The valve leaflets 104, 106, 108 are designed with a customized variable thickness (discussed in greater detail below) for the reduction of high stress concentrations, and with maximized flexibility. Regions of expected high stress are thickened, that is they have a larger cross section or thickness measurement. Regions of expected lower stress are thinned, that is they have a smaller cross section or thickness. Thereby, the leaflets achieve an optimized stress distribution. The result of the customized variable thicknesses of the leaflets is improved hemodynamics and high durability. The enhanced hemodynamics of the valve 100 result in a lower thrombogenic potential. Embodiments of the valve according to the present invention are shown in FIGS. 4, and 8.

Referring to FIGS. 5 and 6, an operative end 120 of one of the leaflets is depicted wherein the multiple thicknesses of portions of the leaflet are shown. The operative end 120 includes an edge with a cross sectional area that provides thickness measurements for the related portion of the leaflet. The operative end 120 generally corresponds to the operative end of leaflet 106 as can be seen in comparison to the valve is FIG. 4. The portions 122, 134 of the end 120 are at the upper most and lower most portions of the end 120. For example, in one embodiment of the invention, the thicknesses of portions of the leaflet are as follows below. The thicknesses of the portions 122, 134 are in the range of 0.1 mm to 0.35 mm, and may be about 0.25 mm. The thicknesses of portions 122, 134 may be from 0.2 to 0.25 mm with a plus or minus variation of 0.1 mm. A reference point 132 (representing a longitudinal axis passing through the center of the valve 100) is about 9.5 mm from the upper end 122 of the operative end 120, and the reference point 132 is about 13 mm from the lower edge 134 of the operative end 120. From top to bottom, portion 124 of the operative edge is about 0.18 mm thick; portion 126 is about 0.20 mm thick; portion 128 is about 0.25 mm thick; and portion 130 is about 0.18 mm thick. The thicknesses of the operative end 120 regarding portions 126, 128, 130, may be varied in thickness by plus or minus 0.1 mm from the above thicknesses. The leaflets 104, 106, 108 are curved. Leaflets 104, 108 are concave in the same direction so as to fit together as shown in FIG. 4. Leaflet 106 is concave in a complimentary direction to leaflet 104.

In another embodiment of the invention, the leaflets may have a flat profile. A flat profile provides a larger coaptation surface for improved mating of surfaces, which may reduce regurgitation.

Referring to FIG. 6A, the operative end 120 of on of the leaflets is depicted wherein another embodiment of the multiple thicknesses of portions of the leaflet are shown. As in FIG. 6, the portions 122, 134 of the end 120 are at the upper most and lower most portions of the end 120. The thicknesses of the portions 122, 134 may be about 0.15 mm. A post point 132 (representing the post 114 placement in FIG. 6) is about 9 mm from the upper end 122 of the operative end 120, and the post point 132 is about 12 mm from the lower edge 134 of the operative end 120. From top to bottom, portion 124 of the operative edge is about 0.08 mm thick; portion 126 is about 0.10 mm thick; portion 128 is about 0.15 mm thick; and portion 130 is about 0.08 mm thick.

Referring to FIG. 6B, the operative end 120 of on of the leaflets is depicted wherein another embodiment of the multiple thicknesses of portions of the leaflet are shown. As in FIG. 6, the portions 122, 134 of the end 120 are at the upper most and lower most portions of the end 120. The thicknesses of the portions 122, 134 may be about 0.35 mm. A post point 132 (representing the post 114 placement in FIG. 6) is about 9 mm from the upper end 122 of the operative end 120, and the post point 132 is about 12 mm from the lower edge 134 of the operative end 120. From top to bottom, portion 124 of the operative edge is about 0.28 mm thick; portion 126 is about 0.30 mm thick; portion 128 is about 0.35 mm thick; and portion 130 is about 0.28 mm thick.

Referring to FIG. 6C, the operative end 120 of on of the leaflets is depicted wherein another embodiment of the multiple thicknesses of portions of the leaflet are shown. As in FIG. 6, the portions 122, 134 of the end 120 are at the upper most and lower most portions of the end 120. The thicknesses of the portions 122, 134 may be about 0.2 mm. A post point 132 (representing the post 114 placement in FIG. 6) is about 9 mm from the upper end 122 of the operative end 120, and the post point 132 is about 12 mm from the lower edge 134 of the operative end 120. From top to bottom, portion 124 of the operative edge is about 0.20 mm thick; portion 126 is about 0.25 mm thick; portion 128 is about 0.30 mm thick; and portion 130 is about 0.20 mm thick.

Referring to FIG. 7A, shows leaflets 104, 108, with leaflet 104 having a 60 degree angle 115 from a midline of the leaflets to an edge of the leaflet 104. FIG. 7B shows an embodiment of a stent 110 with illustrative dimensions. A dimension 154 from top of the stent 110 to the top of the post 114 is about 10 mm. Dimension 152 is from a vertical outer wall of the post 114 to a reference line inside the valve 100 depicted by reference geometry 156. Dimension 164 is about 16 mm and extends between the post dimensions, including dimension 152, following the reference geometry 156. Radius 160 shows an approximately 5 mm radial dimension from a post to the top of the stent 110 along a valley portion 158 between two posts 114.

Referring to FIG. 7C, an alternative embodiment of a stent 110A portion of a valve according to the invention includes posts 114 being offset from a vertical axis 174, such that the posts extend outwardly from the vertical axis 174 and at an obtuse angle in relation to the base of the stent 110A. Vertical axis 172 passes through the center of the stent, and is shown for reference.

The heart valve of the present disclosure can be surgically implanted in the patient via open heart surgery. Alternatively, the valve may replace a valve in the patient using a catheter delivery system, such as transcatheter valve implantation. An example of a catheter delivery system is disclosed in PCT Application number PCT/US2009/035121, international filing date of Feb. 25, 2009, publication number WO/2009/111241.

The heart valve 100 may also be used in a valve in an artificial heart, as well as for traditional open-heart valve implantation of a heart valve replacement in a patient. The heart valve 100 may also be used in an artificial heart, or in other pulsatile mechanical circulatory support devices (e.g., a left ventricular assist device).

Thereby, the present invention provides optimized leaflet thickness (geometry), and a improved valve stent geometry. The combination of the leaflet geometry, stent geometry, and polymer characteristics provides greater valve stent flexibility, and leaflet durability, resulting in improved leaflet thrombogenicity.

A design methodology includes a design, evaluation, and optimization method, which may be called Device Thrombogenicity Emulator (DTE). DTE includes using a combination of state-of-the-art numerical and experimental methods to virtually assess hemodynamics, and then experimentally verify those results with bench top platelet activation studies. An example of an optimizing methodology applicable to the present invention is described in a paper entitled, "Device Thrombogenicity Emulator (DTE)—Design Optimization Methodology for Cardiovascular Devices: A study in two bileaflet MHV designs"; by Xenos et al.; published in the Journal of Biomechanics, 2010. In the DTE method, it is understood that platelets are annucleate cells that contribute to the formation of blood clots. When they are activated by disturbed blood flow, such as that created by implanted devices, they become sticky and clump together which can lead to stroke or death. The DTE method employs two-phase (fluid and particles) computational fluid dynamics in which is simulated blood flow with the addition of thousands of platelet sized particles. Then, the DTE method calculates the stress accumulation on the particles as they pass through the device and extracts dynamic stress history waveforms from selected "hot-spot" regions of high shear stress suspected to cause platelet activation. The dynamic stress history waveforms can be emulated in a Hemodynamic Shearing Device (HSD). A chromogenic assay may be used to measure thrombin generation, which is a key marker of the platelet activation state. Additionally, finite element analysis may be used to perform fluid-structure interaction studies to generate information about the structural stress developed in relation to blood flow. All of this information is fed into the design process and can be repeated iteratively until the design is optimized. All numerical work may be three-dimensional using the latest material models, including performing uniaxial tensile testing of xSIBS for input into numerical material models.

FIGS. 9 and 11 show the prior art valve stent with uniform thickness leaflets. Optimized variable thickness leaflets according to the invention are shown in FIG. 10. In FIGS. 9 and 10 shown simulations which were conducted with identical material models and mesh densities in order to ascertain the effects of the changes in leaflet geometry. By comparison, FIG. 10 shows reduced stress concentrations and magnitudes. In FIG. 11, the material model was changed to reflect the prior art composite leaflet design, while in FIG. 10 the material model reflected the new xSIBS. The comparison of FIGS. 10 and 11 shows the combined effects of material and geometry changes. The result is that the modified leaflet geometry made from xSIBS produced lower stresses. FIGS. 12-15 represent mesh dependency studies and show consistent stress patterns over different mesh densities in the prior art stent geometry with both uniform thickness composite leaflets and new customized thickness leaflets with corresponding material models, both prior composite and new xSIBS. FIGS. 16, 17 show the effects of a flexible stent on the stress distribution in the leaflets using the prior art stent geometry with both uniform thickness composite leaflets in FIG. 16 with a prior art composite material, compared to customized thickness leaflets with corresponding material models of the present invention of FIG. 17, with xSIBS material. A flexible stent made of xSIBS produced low stresses.

Figure 19:
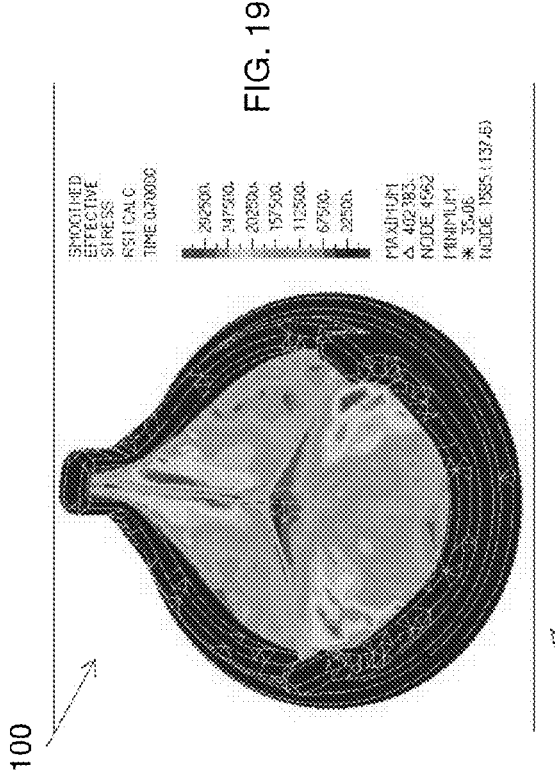
Figure 18:
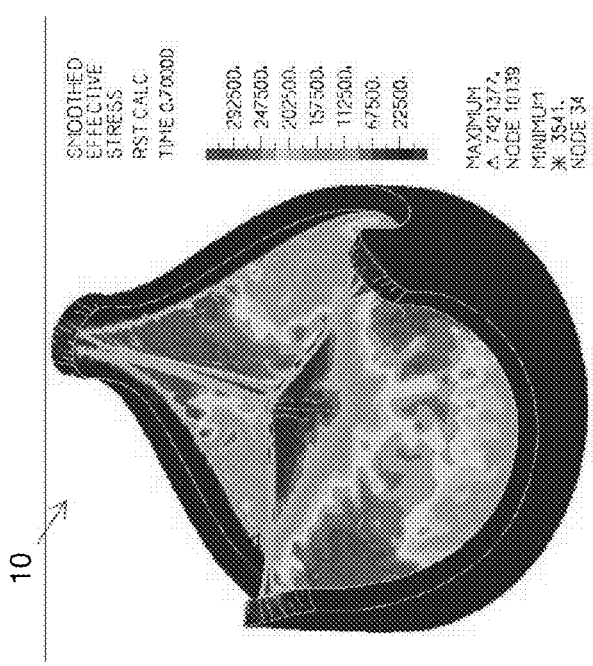

Valves shown in FIGS. 18 and 19 depict a comparison of stent design changes. The stent shown in FIG. 18 incorporates some of the features of the present disclosure, and new stent geometries are shown in stent of FIG. 19. Both the valves shown in FIGS. 18 and 19 have customized thickness leaflets and the xSIBS material model. The new stent design (geometries) shown in FIG. 19 produced lower stresses in the leaflets.

Figures 20, 21:
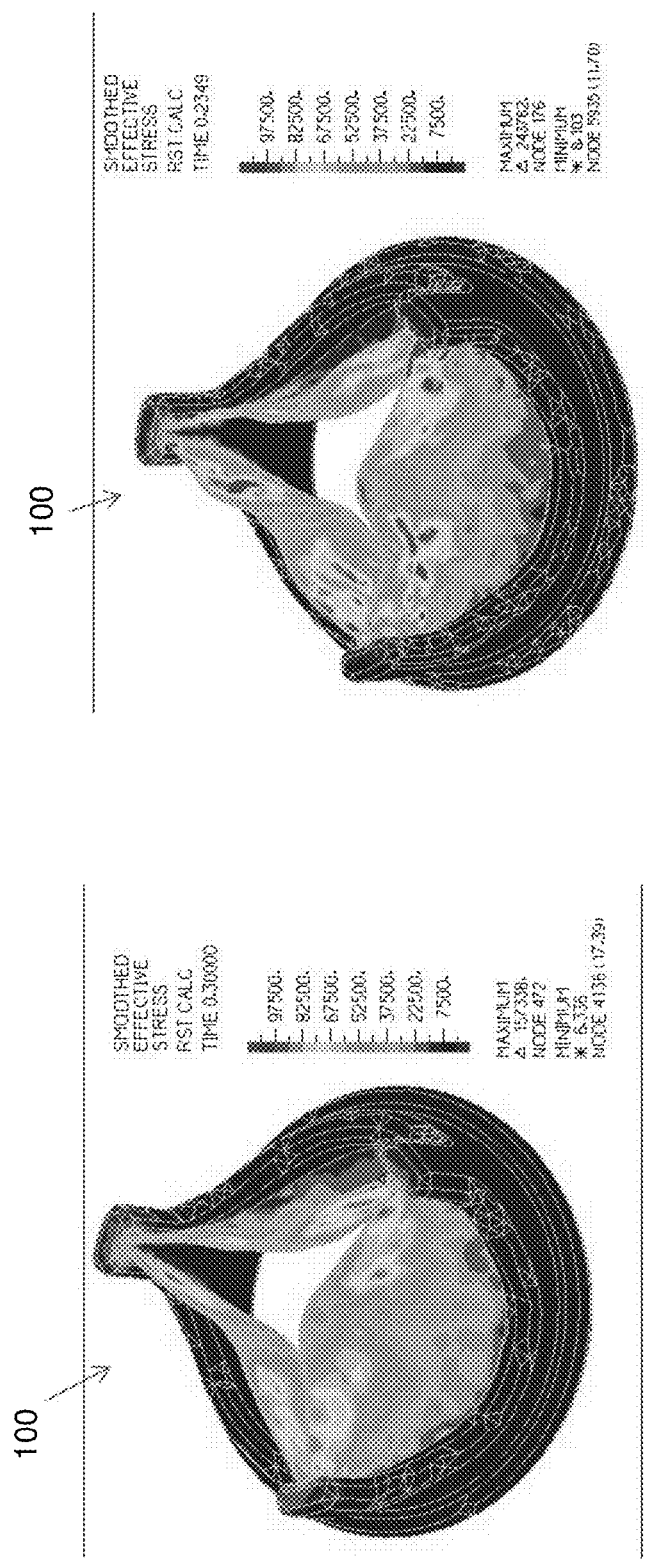
Figure 22:
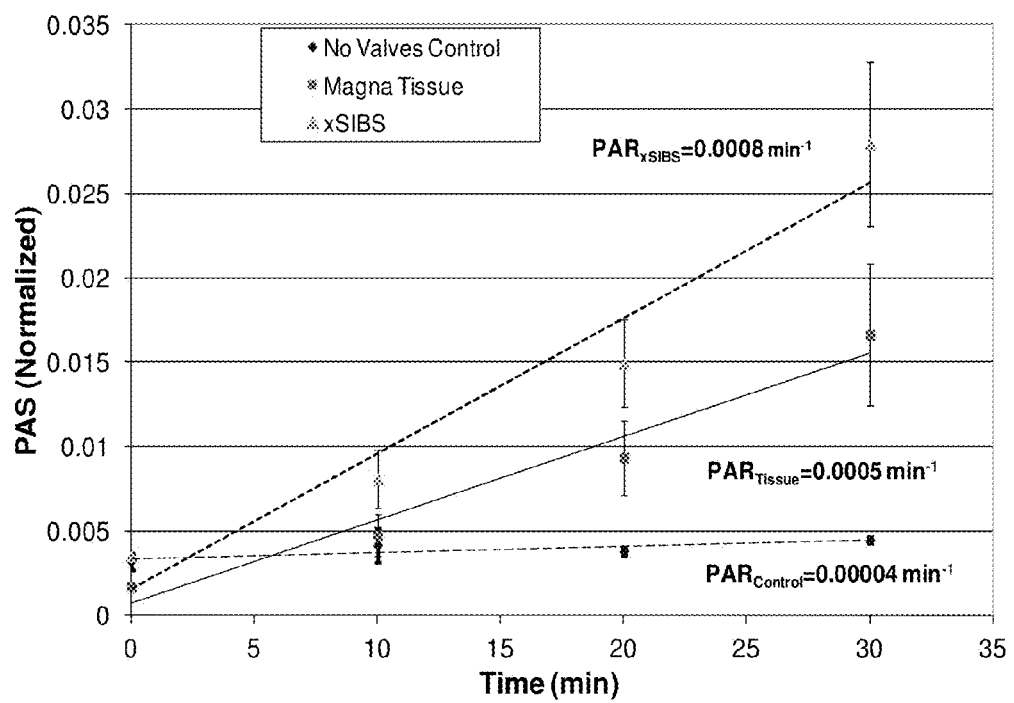
FIG. 22 is a graph showing bulk human platelet activation measurements. Polymer xSIBS valve v. Carpientier-Edwards Perimount Magna tissue valve (benchmark 'gold standard' tissue valve).
Figure 23:
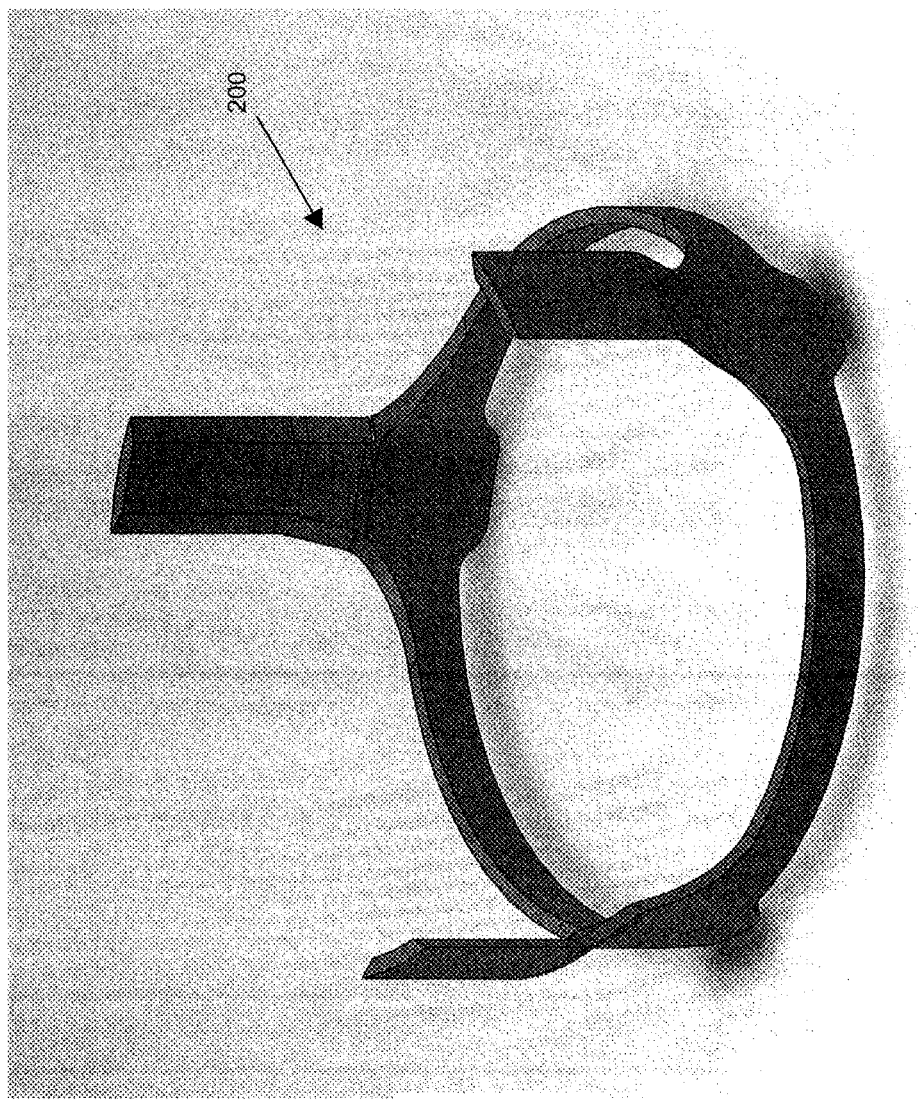
FIG. 23 is an isometric view of the reinforcing frame.

FIGS. 20 and 21 show a comparison of stent design changes wherein the stent shown in FIG. 20. Both the stents shown in FIGS. 20 and 21 include customized thickness leaflet and the xSIBS material according to the present invention. The leaflets of the valves are in semi-open valve positions. The stent design according to the present invention produced lower stresses in the leaflets. All numerical results in FIGS. 9-21 are shown with identical stress scales.

While the present invention has been particularly shown and described with respect to preferred embodiments thereof, it will be understood by those skilled in the art that changes in forms and details may be made without departing from the spirit and scope of the present application. It is therefore intended that the present invention not be limited to the exact forms and details described and illustrated herein, but falls within the scope of the appended claims.

EXAMPLE

Platelet thrombin generation rates were measured using a platelet activation state (PAS) assay. Results were compared measurements conducted with 21 mm Carpentier-Edwards Perimount Magna tissue valves mounted in the pulsatile LVAD and to a negative control, in which the LVAD was run without valves.
Bulk Human Platelet Activation Measurements Platelet activation of the valves was measured using 120 ml of blood. A Berlin pulsatile left ventricular assist device (LVAD) was used to recirculate 250 ml of solution containing freshly isolated human platelets at a concentration of 20,000/μl in platelet buffer. The system held two identical valves mounted inside custom designed valve holders oriented in opposite directions. The inflow and outflow ports were connected with a compliance reservoir. The pump rate was set to 90 BPM with a stroke volume of 65 ml, corresponding to a cardiac output (CO) of 5.85 l/min. The systole/diastole ratio was set to 0.375. The recirculation test was run for 30 min with samples taken in duplicate every 10 min. Platelet thrombin generation rates were measured using our platelet activation state (PAS) assay. Results were compared to previous measurements (n=6) conducted with 21 mm Carpentier-Edwards Perimount Magna tissue valves mounted in the same LVAD and to a negative control, in which the LVAD was run without valves. One-way ANOVA statistics were performed on the platelet activation rates (PAR)—the slope of the PAS measured over the 30 min. recirculation experiments, calculated from a linear best fit curve for each experiment with significance level $\alpha=0.05$.

There was no significant statistical difference between the platelet activation rates (PAR) of the tissue valve (PAR=0.0005 $min^{-1}$) and the xSIBS valve (PAR=0.0008 $min^{-1}$), although the xSIBS valve exhibited a trend of a slightly higher PAR. Both valves PAR's were significantly different from the control (p<0.05). This indicates that the optimized xSIBS valve may not require anticoagulants since the tissue valves used for comparison do not cause clinically significant thrombosis.

What is claimed is:

1. A polymeric valve, comprising:
   a stent having a base and a plurality of outwardly extending posts from the base which are substantially equidistant from each other; and
   a plurality of leaflets each connected to a corresponding one of the posts at one end, and each of the leaflets connected to the base, each of the leaflets having an operative end opposite the end connected to the post, the operative ends of the leaflets being biased in a closed position such that the operative ends abut each other, the operative ends being configured to rhythmically open and close in relation to each other, and the leaflets including multiple cross sectional thicknesses at different portions of the leaflets,
wherein the leaflets are connected to the base at a first end, and comprise a middle portion between the first end and the operative end,
wherein a first portion between the first end and the middle portion is thinner than the first end,
wherein the middle portion is about the same thickness as the first end,
wherein a second portion between the middle portion and the operative end is about the same thickness as the first portion,
wherein the operative end is about the same thickness as the first end,
wherein the leaflets comprise a polymer material of multiple cross sectional thicknesses, and
wherein the first end, the first portion, the middle portion, the second portion and the operative end are aligned from the first end to the operative end.

2. The valve of claim 1, wherein the plurality of outwardly extending posts comprise three outwardly extending posts.

3. The valve of claim 1, wherein the posts are positioned about 8 mm to 10.5 mm from the operative end of each of the leaflets, respectively.

4. The valve of claim 1, wherein the posts are positioned about 8 mm from the operative end of each of the leaflets, respectively.

5. The valve of claim 1, wherein the posts are positioned about 8.5 mm from the operative end of each of the leaflets, respectively.

6. The valve of claim 1, wherein the posts are positioned about 9 mm from the operative end of each of the leaflets, respectively.

7. The valve of claim 1, wherein the posts are positioned about 9.5 mm from the operative end of each of the leaflets, respectively.

8. The valve of claim 1, wherein the posts are positioned about 10 mm from the operative end of each of the leaflets, respectively.

9. The valve of claim 1, wherein the posts are positioned about 10.5 mm from the operative end of each of the leaflets, respectively.

10. The valve of claim 1, wherein the posts extend at a greater angle than 90 degrees from a horizontal plane defined by the base, and the posts extend at an obtuse angle in relation to the base of the stent.

11. The valve of claim 1, wherein the valve is a heart valve.

12. The valve of claim 1, wherein the valve is a trileaflet heart valve.

13. The valve of claim 1, wherein the valve comprises xSIBS material.

14. The valve of claim 1, wherein the posts have substantially rounded edges of a substantially rectangular top portion.

15. The valve of claim 1, wherein the base of the stent includes a hemispherical ridge extending around a perimeter of the base.

16. The valve of claim 1, wherein the multiple thicknesses of the leaflets include thicknesses in the range of about 0.25 mm to about 0.18 mm.

17. The valve of claim 1, wherein the multiple thicknesses along an edge of the operative end of the leaflets include thicknesses in the range of about 0.25 mm to about 0.18 mm.

18. The valve of claim 1, wherein the middle portion including the operative end of the leaflets has a thickness of about 0.25 mm.

19. The valve of claim 1, wherein the first portion and the second portion have a thickness of about 0.20 mm.

20. The valve of claim 1, wherein the stent includes a metal reinforcing frame being embedded in the stent.

21. The valve of claim 20, wherein the metal reinforcing frame includes stainless steel.

22. The valve of claim 1, wherein the thickness of each of the first end, the first portion, the middle portion, the second portion and the operative end extend along a width of the leaflet between the outwardly extending posts.

23. A method for manufacturing a heart valve using injection molding, comprising:
configuring a stent having a base and a plurality of outwardly extending posts from the base;
configuring a plurality of leaflets each connected to a corresponding one of the posts at one end, and each of the leaflets connected to the base;
molding each of the leaflets having an operative end opposite the end connected to the post, and the operative ends of the leaflets are biased in a closed position such that the operative ends abut each other, wherein the leaflets are connected to the base at a first end, and comprise a middle portion between the first end and the operative end, wherein a first portion between the first end and the middle portion is thinner than the first end, wherein the middle portion is about the same thickness as the first end, wherein a second portion between the middle portion and the operative end is about the same thickness as the first portion and wherein the operative end is about the same thickness as the first end, wherein the leaflets comprise a polymer material of multiple cross sectional thicknesses, wherein the first end, first portion, middle portion, second portion and operative end are aligned from the first end to the operative end;
configuring the operative ends to rhythmically open and close in relation to each other;
molding the leaflets including multiple thicknesses of cross sectional areas at different portions of the leaflets; and
heating a resulting mold derived from the steps above.

24. The method of claim 23, wherein the mold includes three leaflets to configure a trileaflet heart valve.

25. The method of claim 23, wherein the thickness of each of the first end, the first portion, the middle portion, the second portion and the operative end extend along a width of the leaflet between the outwardly extending posts.

* * * * *